United States Patent [19]

Barabas

[11] Patent Number: 4,713,238

[45] Date of Patent: Dec. 15, 1987

[54] WATER SOLUBLE COMPLEX OF A POLY (VINYL LACTAM) AND CHLOROTHIAZIDE AND PROCESS FOR PRODUCING SAME

[75] Inventor: Eugene S. Barabas, Watchung, N.J.

[73] Assignee: GAF Corporation, Wayne, N.J.

[21] Appl. No.: 858,635

[22] Filed: May 2, 1986

[51] Int. Cl.$^4$ .................... A61K 31/38; C07D 285/28
[52] U.S. Cl. ........................................ 424/80; 424/78; 514/222; 514/225; 514/929; 544/13
[58] Field of Search .................. 544/13; 514/222, 225, 514/929; 424/78, 80

[56] References Cited

U.S. PATENT DOCUMENTS

| | | | |
|---|---|---|---|
| 4,291,015 | 9/1981 | Keith et al. | 514/929 |
| 4,431,644 | 2/1984 | Smith et al. | 544/13 |
| 4,559,340 | 12/1985 | Neustadt et al. | 544/13 |

OTHER PUBLICATIONS

Merck et al, Merck & Co. Inc., 9th Ed., 1976, Rahway, N.J., U.S.A., p. 277.
Masaki et al, CA, vol. 77, 1972, 77:164547z.
Copes et al, CA, vol. 79, 1973, 79:18562a, p. 439.

*Primary Examiner*—Henry R. Jiles
*Assistant Examiner*—J. G. Mullins
*Attorney, Agent, or Firm*—Marilyn J. Maue; Joshua J. Ward

[57] ABSTRACT

The invention relates to the novel water soluble chlorothiazide in a complexed state which is derived from the reaction between and N-Vinyl actam polymer and chlorothiazide in alkaline media and to the process for the preparation of said complex.

12 Claims, No Drawings

WATER SOLUBLE COMPLEX OF A POLY (VINYL LACTAM) AND CHLOROTHIAZIDE AND PROCESS FOR PRODUCING SAME

Chlorothiazide(6-chloro-7-sulfamyl-1,2,4-benzothiadiazine-1,1-dioxide) is a antihypertensive and diuretic drug which is also used to treat congestive heart failure in animals. However, administration of this compound in solution is complicated by its low water-solubility, i.e. 0.5 g. per liter at pH 6. Although this drug is soluble in alkaline aqueous solutions, it decomposes rapidly on standing. Because of its application in pharmaceutical areas, it is important that no solvent having toxic or other deleterious side effects be employed for its medicinal use in solution.

Accordingly, it is an object of the present invention to provide chlorothiazide in a highly water soluble form with no objectionable side effects.

Another object of this invention is to provide a commercially feasible process for the production of chlorothiazide in highly water soluble form.

These and other objects of the invention will become apparent from the following description and disclosure.

According to this invention there is provided a complexed water soluble product derived from the reaction between a N-vinyl lactam polymer of from 6 to 7 carbon atoms, such as poly(N-vinyl-2-pyrrolidone), poly(N-vinylcaprolactam) or mixtures thereof and chlorothiazide. This product is a true complex containing repeating complexed chlorothiazide/vinyl pyrrolidone units.

The complexed product of this invention may also contain non-complexed vinylpyrrolidone moiety sites of the general formula:

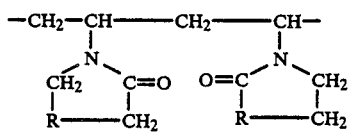

wherein R is —$CH_2$— or —$C_2H_4$—.

It is most probable that the bonding between the polymer and the chlorothiazide drug takes place through hydrophobic bonding in which the aromatic moiety of the drug compound and the hydrocarbon chain of the poly(vinyl pyrrolidone) are responsible for the complexing interaction. The hydrophobic bonding force will bring the drug molecules and the polymer chain in close contact where short range dispersion forces become operative and contribute to the stabilization of the complex. While complexation through hydrogen bonding between the carbonyl group of the pyrrolidone ring and the proton present in the cyclic imino donor of the drug cannot be entirely excluded, the probability of such effect is small, under the conditions of the reaction and the initial formation of a salt. However, once the salt is destroyed, hydrogen bonding becomes more possible.

The scope of this invention is not to be restricted by theoretical considerations with respect to the nature of the complex bonding since it will be recognized that the ability of the compound to be complexed and solubilized by poly(vinyl pyrrolidone) depends to a great extent upon the chemical, physical and morphological characteristics of the compound, the hydrophilic-hydrophobic ratio of its structural elements, the nature and relative position of its substituents, the bulkiness of the molecule in general and the substituents in particular. Small difference in any of the above factors may significantly alter the solubilizing capability. While the complexability of the compound with poly(vinylpyrrolidone) may be predicted to some extent, on the chemcial character of its substituents, its solubility cannot be predicted on structural similarities alone. Instead a combination of aforesaid factors interacting between the compound to be complexed and the polymer must be considered. Thus, each compound must be viewed and tested individually for a determination of its solubility. To illustrate the above discussion, a compound having solubility parameters similar to chlorothiazide, including good solubility in alkali hydroxides, is represented by chlorzoxazone, i.e.

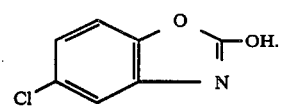

This compound has a phenolic-type hydroxyl substituent, which complexes readily with poly(vinylpyrrolidone). Nevertheless, the coprecipitate of this compound with poly(vinylpyrrolidone) was found to be insoluble in water, while the coprecipitate of chlorothiazide showed good water solubility.

The complexed units in the polymer may occur in block, random or alternating distribution. In any case, the resulting product contains at least about 10 wt. % up to 30 wt. %, complexed units. Generally at least 90 wt. % of the chlorothiazide employed, or an amount sufficient to retain the properties of the drug, is complexed in the product. The complexed state of chlorothiazide has been established by experiment showing that at gradual dilution from 2% to 0.01% in water, no free chlorothiazide precipitates from the aqueous solution. If a complex had not formed, the chlorothiazide would precipitate out of solution in this range of dilution. A complex water solubility of at least 15% is desired and water solubility as high as 25% has been achieved. That the material remains in solution at high dilution, significantly above the solubility limit of uncomplexed chlorothiazide, i.e. 0.05% at room temperature, is indeed unexpected.

While the complexes of the invention are stable under normal conditions, they are subject to in vivo hydrolytic forces and other physical chemical effects which lead to slow dissociation. Therefore these complexes can function as slow release systems suitable for the sustained delivery of the drug portion of the complex in medical and veterinarial applications.

The product of this invention preferably contains complexed and un-complexed N-vinyl-2-pyrrolidone units derived from poly(N-vinyl-2-pyrrolidone) having a K value between 12 and 30; although polymers of K-6 to K-90 may also be employed in certain cases. Polymers of K-100 or more, becuase of their high solution viscosity, may limit the amount of chlorothiazide which they can bring into solution in complexed form.

The chlorothiazide in the complexed state of this invention is generally present in an amount of from about 10 wt. % to about 30 wt. %, preferably from about 12 wt. % to about 15 wt. %, and exhibits at least a 50 fold increase in water solubility over the uncomplexed compound.

The chlorothiazide complex of this invention is prepared by a relatively simple and direct process which involves separately dissolving both the chlorothiazide and the N-vinyl lactam polymer in an aqueous alkali metal hydroxide solution, e.g. a 1.8% to 5% sodium or potassium hydroxide solution to provide solutions wherein each reactant is present in between about 5 and about 25 weight % concentration preferably between about 8% and about 15% by weight concentration of active components.

The N-vinyl lactam reactant in the complexing reaction is one having the formula

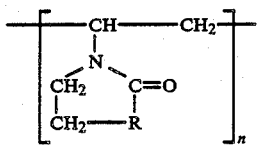

where R is as defined above and n is an integer having a value of from 5 to 3,500.

The solutions of the reactant species are then combined in a mole ratio of poly-N-vinyl lactam:chlorothiazide of between about 1:1 and about 10:1, preferably in a ratio of 4-7:1, and thoroughly mixed under atmospheric pressure, or superatmospheric pressure up to 50 psig, at a temperature above 3° C. and below the boiling point of the hydroxide solution which includes a range of between about 4° C. and about 100° C., preferably between about 10° C. and about 40° C. The mixture, which is at a pH of between about 7.5 and 10, preferably between about 8 and 9, is agitated under these conditions for a period of from about 5 minutes to about 3 hours, more often between about 10 and about 30 minutes to effect the complexing reaction which produces the alkali salt of the complexed compound.

After completion of the reaction, or complexing to the degree desired, the resulting liquid mixture comprising the alkali metal salt of the complex and aqueous alkali metal hydroxide solvent is treated to remove solvent by any conventional means, such as rotary evaporation or freeze drying. Evaporation is conducted in vacuo, e.g. under a pressure of from about 2 to about 40 mm Hg, preferably not more than 25 mm Hg. The complexed salt solution is recovered and dried at a temperature between about 45° C. and about 100° C., preferably between about 50° C. and about 65° C. in vacuo for a period of 1 to 24 hours to produce a solid salt complex.

The dried complex is then mixed with water and the pH adjusted to between about 3.5 and about 7, preferably between about 5 and about 6.3 with a mineral acid, preferably hydrogen chloride as a 1.8-5% concentrated aqueous solution, to convert the complexed alkali metal salt of the sulfamyl group to sulfamyl radical so as to produce the complexed product of the invention.

The resulting chlorothiazide in this complexed form is stable and is found to have a water solubility increased from about 0.05% to at least 15% or more at room temperature.

Having thus generally described the present invention, reference is now had to the following examples which illustrate preferred embodiments but which are not to be construed as limiting to the scope of the invention as more broadly set forth hereinabove and in the appended claims.

EXAMPLE 1

Chlorothiazide (5 grams) was dissolved in 45 grams of a 2% aqueous solution of sodium hydroxide and the solution added to a dropping funnel. Poly(N-vinyl-2-pyrrolidone), K-30 (20 grams) was separately dissolved in 180 grams of an aqueous 2% sodium hydroxide solution and poured into a separate dropping funnel. 50 grams of the chlorothiazide solution and 200 grams of the polyvinylpyrrolidone solution were charged dropwise over a period of 15 minutes to a 500 milliliter flask and the resulting solution agitated for 15 minutes at room temperature. The pH of the reacting mixture was about 8.5 and the complex formed with the sodium salt of poly(N-vinyl-2-pyrrolidone) and chlorothiazide.

The liquid reaction medium is then evaporated under about 20 mm Hg to remove the solvent and the resulting solid was dried under similar vacuum at 60° C. overnight.

In a screwcap jar, 2 grams of the above salt complex was agitated on a horizontal shaker at room temperature with 20 grams of distilled water, corresponding to 2.2% of the complex. After about ½ hour a clear solution was obtained and the pH was adjusted to 5.5 with concentrated hydrochloric acid solution. The polymer-chlorothiazide complex remained in solution at the acid pH.

An additional 2 grams of the salt complex was added to the clear liquid, thus raising the concentration of chlorothiazide to 4.3%. The pH was again adjusted to about 6 without the appearance of haze. The step of additional 2 gram additions with adjustment of the pH to the acid side was repeated 8 times until a total of 20 grams of the polymer-chlorothiazide complex was reached, corresponding to 16.2% solution of chlorothiazide in water.

As a control, chlorothiazide (1 gram) was placed in a screwcap jar, where it is mixed with 90 grams of distilled water. The pH was adjusted with a buffer solution to 6 and distilled water was added to bring the solution to 1% concentration. The resulting mixture was agitated on a horizontal shaker at room temperature for 24 hours. After this period the water solubility of the chlorothiazide solid which remained in the aqueous solution was found to be 0.05%.

EXAMPLE 2

Chlorothiazide (5 grams) and poly(vinylpyrrolidone) K-15 (20 grams) respectively, were dissolved in 2% aqueous sodium hydroxide to form 10% solutions. These solutions were mixed and the mixture were dried as described in Example 1. The product was the sodium salt of the poly(vinylpyrrolidone)-chlorothiazide complex.

The complex sodium salt solid (20 grams) was placed in a screwcap jar wherein it was agitated on a horizontal shaker with 18.0 grams of distilled water for a period of ½ hour. The pH was then adjusted to 6.5 with a concentrated aqueous hydrochloric acid solution to convert the complexed salt to the complexed product of the process and agitation was continued for 2 hours. At the end of this period, a clear solution having a pH of 6.5 was obtained and the water solubility of the chlorothiazide in the complex was found to be 16.2%.

EXAMPLE 3

Example 1 was repeated except that dimethyl formamide was substituted for the 2% sodium hydroxide solution. 1 gram of the resulting precipitate containing 0.2 grams of chlorothiazide was added to 99 grams of distilled water. After shaking for 24 hours at room temperature none of the chlorothiazide had dissolved in the water.

Examples 1 and 2 are intended to set forth a preferred embodiment of the present invention; however, many variations and modifications of the above experiments and complexed products will become apparent from the foregoing description and disclosure. For example, other alkali metal hydroxide solvents can be employed and other higher or lower molecular weight poly(N-vinylpyrrolidones) or poly(N-vinyl-caprolactams) or other mole ratios of polymer to chlorothiazide can be substituted to produce complexes wherein the chlorothiazide shows markedly increased water solubility.

What is claimed is:

1. Water soluble chlorothiazide in a complexed state, derived from the reaction between a polymer of a N-vinyl lactam having 6 to 7 carbon atoms and chlorothiazide.

2. The complexed product of claim 1 wherein the N-vinyl lactam is poly(N-vinyl-2-pyrrolidone).

3. The complexed product of claim 2 wherein the complexed product contains between about 10 and about 30 weight % of chlorothiazide.

4. The complexed product of claim 3 wherein the complexed product contains between about 12 and about 15 weight % of chlorothiazide.

5. The complexed product of claim 4 wherein the chlorothiazide is at least 15% soluble in water.

6. The product of claim 2 wherein the poly(N-vinyl-2-pyrrolidone) has a K value between about 12 and about 30.

7. The complexed compound of claim 2 containing complexed chlorothiazide/vinyl pyrrolidone repeating units.

8. The process for producing the complexed compound of claim 1 which comprises: mixing alkali metal hydroxide solutions of chlorothiazide and a poly(N-vinyl lactam) having the formula:

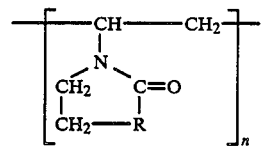

wherein n is an integer having a value of from 5 to 3,500 and R is $-CH_2-$ or $-C_2H_4-$ in a mole ratio of polymer to chlorothiazide of between about 1:1 and about 10:1, agitating the mixture having a pH of between about 7.5 and about 10 under a pressure of from about atmospheric to about 50 psig at a temperature of from about 4° C. to about 100° C. and below the boiling point of said hydroxide solution, for a period of from about 5 minutes to about 3 hours, to form the alkali metal salt of the complexed poly(N-vinyl lactam) and chlorothiazide in the liquid phase, separating said hydroxide solution from said complexed salt, diluting said complexed salt with water and adjusting the pH of the resulting solution to between about 3.5 and about 7 to produce the complexed poly(N-vinyl lactam)-chlorothiazide product of the reaction.

9. The process of claim 8 wherein the poly(N-vinyl lactam) is poly(N-vinyl-2-pyrrolidone) having a K value of from about 6 to about 90.

10. The process of claim 9 wherein the poly(N-vinyl-2-pyrrolidone) has a K value between about 12 and about 30.

11. The process of claim 9 wherein the poly(N-vinyl-2-pyrrolidone) in aqueous alkali metal hydroxide solution is mixed with an aqueous alkali metal hydroxide solution of chlorothiazide in a weight ratio of between about 4:1 and about 7:1 and wherein the mixture having a pH of from 8 to 9 is reacted at a temperature of from about 10° C. to about 40° C. under a pressure of from about 14 to about 50 psig and the pH, after reaction is adjusted to between 5 and 6.

12. The process of claim 11 wherein the reaction is effected under atmospheric pressure and the solvent is a 1.8 to 5% aqueous sodium hydroxide or potassium hydroxide solution.

* * * * *